United States Patent
Hestad et al.

(10) Patent No.: US 8,043,381 B2
(45) Date of Patent: Oct. 25, 2011

(54) MINIMALLY INVASIVE INTERBODY DEVICE AND METHOD

(75) Inventors: Hugh D. Hestad, Edina, MN (US); Robert Garryl Hudgins, Monticello, MN (US); John Maertens, Chanska, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1030 days.

(21) Appl. No.: 11/926,975

(22) Filed: Oct. 29, 2007

(65) Prior Publication Data

US 2009/0112323 A1 Apr. 30, 2009

(51) Int. Cl.
*A61F 2/44* (2006.01)

(52) U.S. Cl. ............... 623/17.16; 623/17.12; 606/90

(58) Field of Classification Search .... 623/17.11–17.16, 623/7, 8; 604/96.01–103.14, 104–109; 606/90, 606/92–94, 192, 195, 202
See application file for complete search history.

(56) References Cited

U.S. PATENT DOCUMENTS

| | | | | |
|---|---|---|---|---|
| 4,433,440 A * | 2/1984 | Cohen | | 623/8 |
| 4,944,749 A * | 7/1990 | Becker | | 623/8 |
| 5,549,679 A * | 8/1996 | Kuslich | | 623/17.12 |
| 5,630,843 A * | 5/1997 | Rosenberg | | 623/8 |
| 5,681,317 A * | 10/1997 | Caldarise | | 606/93 |
| 6,017,350 A * | 1/2000 | Long | | 606/94 |
| 6,332,894 B1 | 12/2001 | Stalcup et al. | | |
| 6,733,533 B1 * | 5/2004 | Lozier | | 623/17.12 |
| 7,563,284 B2 * | 7/2009 | Coppes et al. | | 623/17.12 |
| 7,799,078 B2 * | 9/2010 | Embry et al. | | 623/17.11 |
| 2004/0127992 A1 * | 7/2004 | Serhan et al. | | 623/17.16 |
| 2004/0230309 A1 * | 11/2004 | DiMauro et al. | | 623/17.12 |
| 2004/0236425 A1 * | 11/2004 | Huang | | 623/17.12 |
| 2004/0249462 A1 * | 12/2004 | Huang | | 623/17.13 |
| 2005/0049604 A1 * | 3/2005 | Singer et al. | | 606/90 |
| 2005/0090901 A1 * | 4/2005 | Studer | | 623/17.12 |
| 2005/0119752 A1 * | 6/2005 | Williams et al. | | 623/17.16 |
| 2005/0278027 A1 * | 12/2005 | Hyde, Jr. | | 623/17.12 |
| 2006/0149380 A1 * | 7/2006 | Lotz et al. | | 623/17.12 |
| 2006/0247780 A1 * | 11/2006 | Bert | | 623/17.16 |
| 2006/0265076 A1 * | 11/2006 | Carter et al. | | 623/17.16 |
| 2006/0293749 A1 * | 12/2006 | Hudgins et al. | | 623/17.11 |
| 2006/0293751 A1 * | 12/2006 | Lotz et al. | | 623/17.12 |
| 2007/0038300 A1 * | 2/2007 | Bao et al. | | 623/17.12 |
| 2007/0038301 A1 | 2/2007 | Hudgins | | |
| 2007/0078477 A1 * | 4/2007 | Heneveld et al. | | 606/191 |
| 2007/0135921 A1 * | 6/2007 | Park | | 623/17.12 |
| 2007/0173940 A1 * | 7/2007 | Hestad et al. | | 623/17.12 |

FOREIGN PATENT DOCUMENTS

WO 2006130796 A2 12/2006

* cited by examiner

*Primary Examiner* — Eduardo C Robert
*Assistant Examiner* — Lynnsy Schneider
(74) *Attorney, Agent, or Firm* — Seager Tufte Wickhem LLC

(57) ABSTRACT

Methods and devices for insertion between adjacent vertebrae in a spine following removing at least a portion of a nucleus from within a disc. In one embodiment, the device includes a member having a flexible wall surrounding an internal volume and a coupler that is secured to the flexible wall. The member is adapted to expand when filled with a first filler material to form an interior cavity. The coupler has a first access point, a second access point, a first coupler side hole, and an optional second coupler side hole. The first and second access points are adapted to removably receive one or more fill tubes. The fill tubes cooperate with the first and optional second coupler side holes to direct the first filler material into the internal volume and a second filler material into the interior cavity.

3 Claims, 11 Drawing Sheets

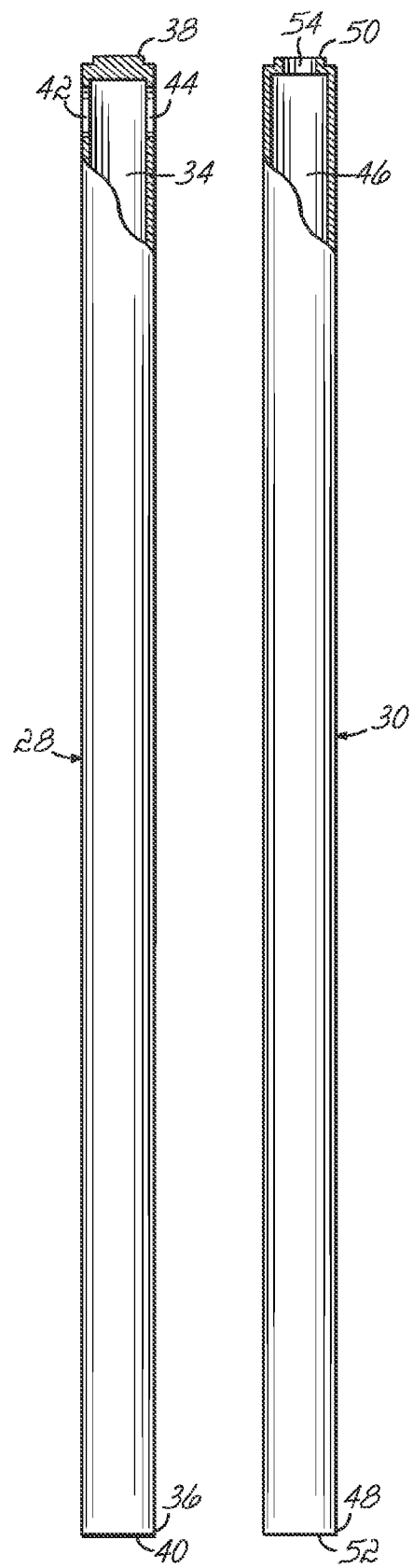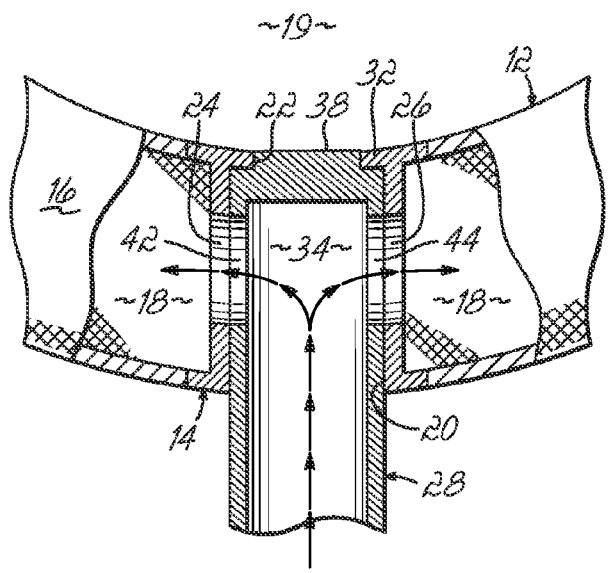
FIG. 5
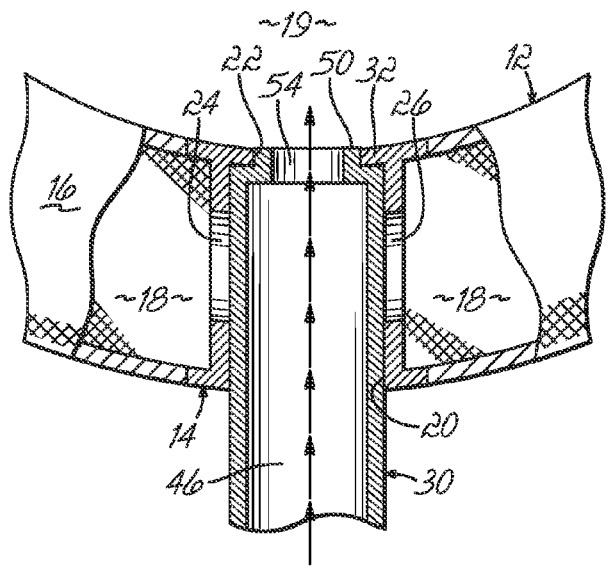
FIG. 6
FIG. 3 FIG. 4

MINIMALLY INVASIVE INTERBODY DEVICE AND METHOD

FIELD OF THE INVENTION

This invention relates to orthopedic implants, and, more particularly, to interbody spinal devices.

BACKGROUND OF THE INVENTION

A spine includes a series of joints or motion segments. The components of each motion segment include two adjacent vertebrae, their apophyseal joints, an intervertebral disc, and connecting ligamentous tissue. Each motion segment is capable of flexion, extension, lateral bending, and translation. Each component of the motion segment contributes to these capabilities and to the mechanical stability of the spine.

The intervertebral disc is one component that facilitates spine motion by allowing slight relative movement between adjacent intervertebral discs as well as holding the vertebrae together. The discs comprise an outer annulus fibrosus which surrounds and contains a nucleus pulposus. The nucleus acts as a shock absorber and a spacer to separate adjacent vertebra. In a healthy spine, the motion segments, including the discs, collectively enable the familiar kinematics of the spinal column. However, degeneration of the disc can cause great and sometimes debilitating pain.

For example, radicular pain in the lower extremities is often a symptom of a herniated disc. A herniated disc is characterized by rupture of or tear in the annulus fibrosus which permits a portion of the nucleus to extrude therefrom. If the nucleus extrudes in proximity to the numerous nerves surrounding the spine, the pressure, or the mere contact, of the nucleus on the nerves may cause severe pain. In addition, axial pain is often a symptom of degenerative disc disease. Degenerative disc disease is generally associated with dehydration of the nucleus that occurs with age. When the nucleus dehydrates, it loses its ability to absorb shock, which may lead to axial pain.

Treatment methods for repair of disc disorders include spinal fusion. One type of spinal fusion procedure requires resection of a portion of the disc. The procedure for removing a portion of the disc is known as a discectomy. Once a portion of the disc is removed, another material or device is inserted into the space created to stabilize the spinal column. There are a variety of devices available for insertion into the disc space. For example, one fusion procedure includes placing a cage between and in contact with the vertebra and packing the cage with graft material. The graft material may bond with the endplates of the adjacent vertebra thus fusing the vertebra together. However, these types of devices require significant retraction of tissue to allow the surgeon sufficient access to the disc and to insert the device into the corresponding disc space. Consequently, patient recovery time may be significant simply because of the invasiveness of these procedures.

Thus, devices and methods for spinal fusion that are stable, yet minimally invasive, are needed.

SUMMARY OF THE INVENTION

The present invention provides an interbody device adapted for insertion between adjacent vertebrae in a spine. In one embodiment, the device comprises a member having a flexible wall surrounding an internal volume and a coupler. The member is adapted to expand when filled with a first filler material to form an interior cavity. The coupler is secured to the flexible wall. The coupler has a first access point, a second access point, a first coupler side hole, and an optional second coupler side hole. The first and second access points are adapted to removably receive one or more fill tubes. The fill tubes cooperate with the first and optional second coupler side holes to direct the first filler material into the internal volume and a second filler material into the interior cavity.

In accordance with another aspect of the invention, an orthopedic system is provided. The orthopedic system is adapted for insertion between adjacent vertebrae in a spine. In one embodiment, the system comprises a member having a flexible wall surrounding an internal volume and a coupler secured to the flexible wall. The member is adapted to expand when filled with a first filler material to form an interior cavity. The coupler has a first access point, a second access point, a first coupler side hole, and an optional second coupler side hole adapted to removably receive one or more fill tubes. The fill tubes cooperate with the first and optional second coupler side holes to direct the first filler material into the internal volume and that cooperate to direct a second filler material into the interior cavity.

In another embodiment, a member fill tube defines a first passage and is adapted for removable cooperation with the coupler via the first access point. When the member fill tube is inserted into the coupler, an opening at a distal end of the member fill tube is in fluid communication with the internal volume via the first passage, the first coupler side hole, and the optional second coupler side hole. In a related embodiment, a cavity fill tube defines a second passage. The cavity fill tube is adapted for removable cooperation with the coupler via the first access point and the second access point. When the cavity fill tube is inserted into the coupler, an opening at a distal end of the cavity fill tube is in fluid communication with the interior cavity via the second passage and the second access point.

In accordance with another aspect of the invention, a method of treating a spine is provided. The method follows forming an incision in an annulus of a disc between adjacent vertebrae and removing at least a portion of a nucleus from within the disc to form a space surrounded by the annulus. The method comprises placing the interbody device within the disc space and then filling the internal volume with the first filler material. In one embodiment, the first filler material comprises a first elastomeric material. Following filling the internal volume, filling the interior cavity with a second filler material. In another embodiment, the second filler material comprises a second elastomeric material. In yet another embodiment, the second elastomeric material is more elastic than the first elastomeric material.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIGS. 3 and 4 are elevation views of embodiments of a member fill tube and a cavity fill tube, respectively, with partial cross sections of a proximal end of each;

FIGS. 5 and 6 are enlarged partial cross sections of the member fill tube of FIG. 3 and the cavity fill tube of FIG. 4, respectively, each individually inserted into the coupler of FIG. 2;

DETAILED DESCRIPTION

Figure 1:
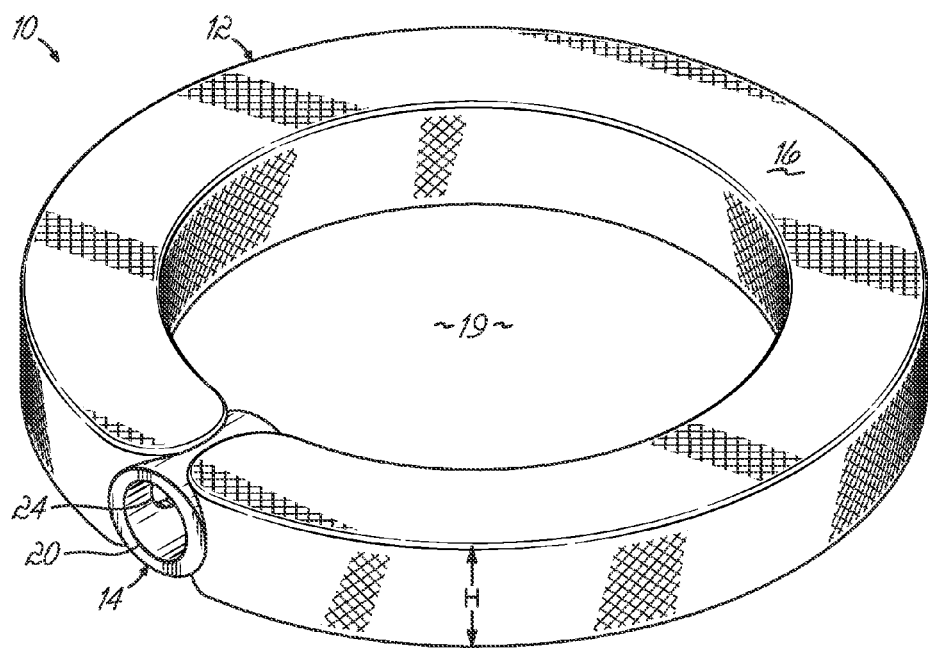
FIG. 1 is a perspective view of one embodiment of an interbody device shown with an member in an expanded state.
Figure 2:
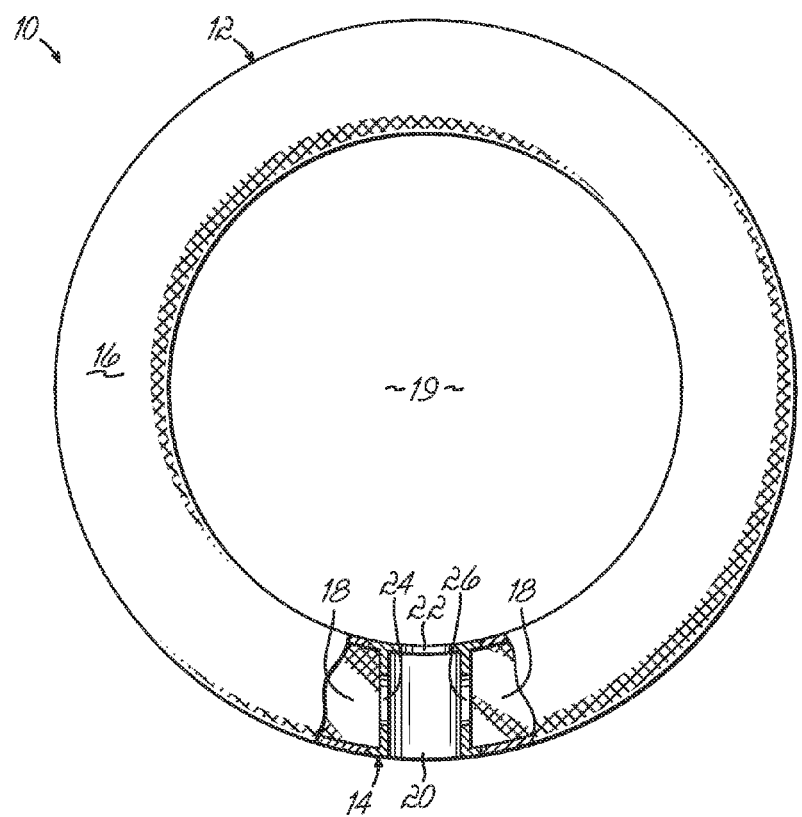
FIG. 2 is a plan view of the interbody device of FIG. 1 with a partial cross section of a coupler and the member.

FIGS. 1 and 2 depict one embodiment of an interbody device 10 of the present invention. As shown, the interbody device 10 comprises a member 12 and a coupler 14. As will be discussed in detail later with reference to FIGS. 7-11, following a partial discectomy, the interbody device 10 is placed between adjacent vertebrae. Once placed, tubes (embodiments of which will be described herein) configured to removably cooperate with the coupler 14 may be used to fill the member 12 with material. In one embodiment, the interbody device 10 facilitates stabilization of a spine and also facilitates stabilization of adjacent vertebrae.

To that end, with reference once again to FIG. 1, the interbody device 10 with the member 12, shown in an expanded state, provides an anatomically contoured shape. While the interbody device 10 has a nearly ring-like perimeter, other shapes and configurations are possible. By way of example and not limitation, the interbody device 10 may be a customized shape designed to accommodate the patient's anatomy, particularly a shape that will treat the patient's physiological problem. Not only may the interbody device 10 have a multitude of shapes, a thickness or height H of the member 12 after it is expanded may vary around its perimeter. For instance, the interbody device 10 may form a wedge-like shape when expanded. Therefore, the interbody device 10 may conform more readily to the patient's anatomy or may facilitate a particular treatment, e.g., the interbody device 10 may be designed to treat degenerative disc disease, stenosis, spondylolisthesis, or other disorder.

With reference to FIG. 2, in one embodiment, the member 12 has a ring-like or annular shape having a flexible wall 16. The flexible wall 16 surrounds an internal volume 18, as shown in the partial cut-away view in FIG. 2. The flexible wall 16 may comprise a polyester, such as Dacron™; a polymethylmethacrylate; a metallic, woven fabric made of titanium, one of its alloys, or a stainless steel; or other suitable biologically compatible material. In one embodiment, the flexible wall 16 is woven, knitted, or braided. Therefore, the annular member 12 may excrete a portion of materials injected therein, as the annular member 12 is expanded to form an interior cavity 19.

As shown in FIG. 2, the coupler 14 is attached to the flexible wall 16. It will be appreciated that the coupler 14 may be attached to the flexible wall 16 via mechanical crimp or clamp, thermal or weld bond, adhesive, or other bonding method known in the art. The coupler 14 may be configured as a tube-like structure to facilitate minimally invasive insertion, as described in detail with regard to FIG. 7. Returning to FIG. 2, the coupler 14 has a first access point 20, a second access point 22, a first coupler side hole 24, and a second coupler side hole 26. In an exemplary embodiment, the first access point 20 is coaxial with the second access point 22. In yet another embodiment, the first coupler side hole 24 opposes the second coupler side hole 26 and both the first and second coupler side holes 24, 26 are orientated transverse to the first and second access points 20, 22.

The access points 20, 22 and side holes 24, 26 cooperate with tubes for directing material within the interbody device 10. For example, as shown in FIGS. 3 and 4, a member fill tube 28 and a cavity fill tube 30, respectively, may be used to direct materials to the coupler 14 for distribution within the annular member 12. Thus, according to another aspect of the present invention and an exemplary embodiment, an orthopedic system comprises the interbody device 10 of FIG. 1, the member fill tube 28 of FIG. 3, and the cavity fill tube 30 of FIG. 4. As shown in FIGS. 5 and 6, which will be discussed in detail below, the first access point 20 slidably receives either the member fill tube 28 of FIG. 3 or the cavity fill tube 30 of FIG. 4, respectively.

In one embodiment, the coupler 14 comprises a rigid material, such as a biocompatible, thermoplastic polymer or biocompatible metal or other similar material. The rigid material does not sag or collapse when the member fill tube 28 is removed from the coupler 14 prior to insertion of the cavity fill tube 30. In other words, the coupler 14 remains open sufficient to receive either tube 28, 30. The rigid material may also ease slidable engagement and removal of the cavity fill tube 30 or reengagement of the member fill tube 28 or cavity fill tube 30 should the surgeon determine that the annular member 12 requires additional material.

In another embodiment, as shown most clearly in FIGS. 5 and 6, the coupler 14 has an annular flange 32. The annular flange 32 may project from the coupler 14 proximate the second access point 22. As shown in FIGS. 5 and 6, in one embodiment, the annular flange 32 may form the second access point 22. One skilled in the art will appreciate that the annular flange 32 may have other configurations, such as one or more protrusions on the coupler 14 that cooperate with one or more depressions on one or both of tubes 28, 30.

With reference to FIGS. 3 and 5, one embodiment of the member fill tube 28 is illustrated in FIG. 3 for directing a filler material into the internal volume 18 within the interbody device 10, as shown in FIG. 5. As shown in FIG. 3, the member fill tube 28 defines a first passage 34 that extends from a distal end 36 to a proximal end 38. The distal end 36 of the member fill tube 28 has an opening 40 formed concentrically with the longitudinal axis of the tube 28 for introducing a filler material into the member fill tube 28. A first tube side hole 42 and a second tube side hole 44 are formed proximate to the proximal end 38, for example transverse to the longitudinal axis. As shown, in one embodiment of the member fill tube 28, the proximal end 38 is closed.

With reference to FIG. 5, the member fill tube 28 is removably inserted into the coupler 14 via the first access point 20. When the member fill tube 28 is positioned within the coupler 14, the first and second tube side holes 42, 44 at least partially align with the first coupler side hole 24 and the optional second coupler side hole 26, respectively. It will be appreciated that the first and second tube side holes 42, 44 as well as the first and second coupler side holes 24, 26 may have different configurations and still facilitate flow of materials from the opening 40 into the internal volume 18. The member fill tube 28 may also substantially block the second access point 22 e.g., with the closed proximal end 38 when the other holes 24, 26, and 42, 44, respectively, are aligned.

In one embodiment, the member fill tube 28 passes through the first access point 20 and docks with the second access point 22. In other words, a portion of the member fill tube 28 cooperates with a portion of the coupler 14. For example, the member fill tube 28 may have the proximal end 38 configured, as shown in FIG. 5, to cooperate with the annular flange 32 projecting from the coupler 14. The cooperative engagement between the annular flange 32 and the proximal end 38 of the member fill tube 28 may provide a tactile "docking" sensation which the surgeon may identify as the proper alignment of the member fill tube 28 within the coupler 14. Proper alignment may include alignment of first and second tube side holes 42, 44 with first and second coupler side holes 24, 26, respectively. Furthermore, the member fill tube 28 has a length that may extend to an accessible location outside the patient to ease filling of the internal volume 18.

Similarly, one embodiment of the cavity fill tube 30 is illustrated in FIG. 4 for directing a filler material into the interior cavity 19 within the interbody device 10, as shown in FIG. 6. As shown, the cavity fill tube 30 defines a second passage 46 that extends from a distal end 48 to a proximal end 50. The distal end 48 of the cavity fill tube 30 has an opening 52 therein for introducing filler material into the cavity fill tube 30, and an axial port 54 is formed in the proximal end 50. Thus the opening 52 is in fluid communication with the axial port 54 via the second passage 46.

With reference to FIG. 6, in the embodiment shown, the cavity fill tube 30 removably and slidably cooperates with the first and second access points 20, 22 in the coupler 14. When the cavity fill tube 30 is positioned within the coupler 14, as shown, the axial port 54 provides fluid communication between the opening 52 and the interior cavity 19 via the second passage 46. Furthermore, the cavity fill tube 30 blocks the first and second coupler side holes 24, 26. In one embodiment, the cavity fill tube 30 passes through the first access point 20 and docks with the second access point 22. In other words, a portion of the cavity fill tube 30 cooperates with a portion of the coupler 14 to align the axial port 54 with the second access point 22 in the coupler 14. For example, the cavity fill tube 30 may have the proximal end 50 configured, as shown in FIG. 6, similar to the proximal end 38 of the member fill tube 28 in FIG. 3, to cooperate with the annular flange 32 projecting from the coupler 14. Similar to the member fill tube 28, the cooperative engagement between the annular flange 32 and the proximal end 50 of the cavity fill tube 30 may provide a tactile sensation which the surgeon may identify as the proper alignment of the cavity fill tube 30 with the coupler 14. Furthermore, the cavity fill tube 30 has a length such that the distal end 48 may extend to an accessible location outside the patient.

Figure 7:
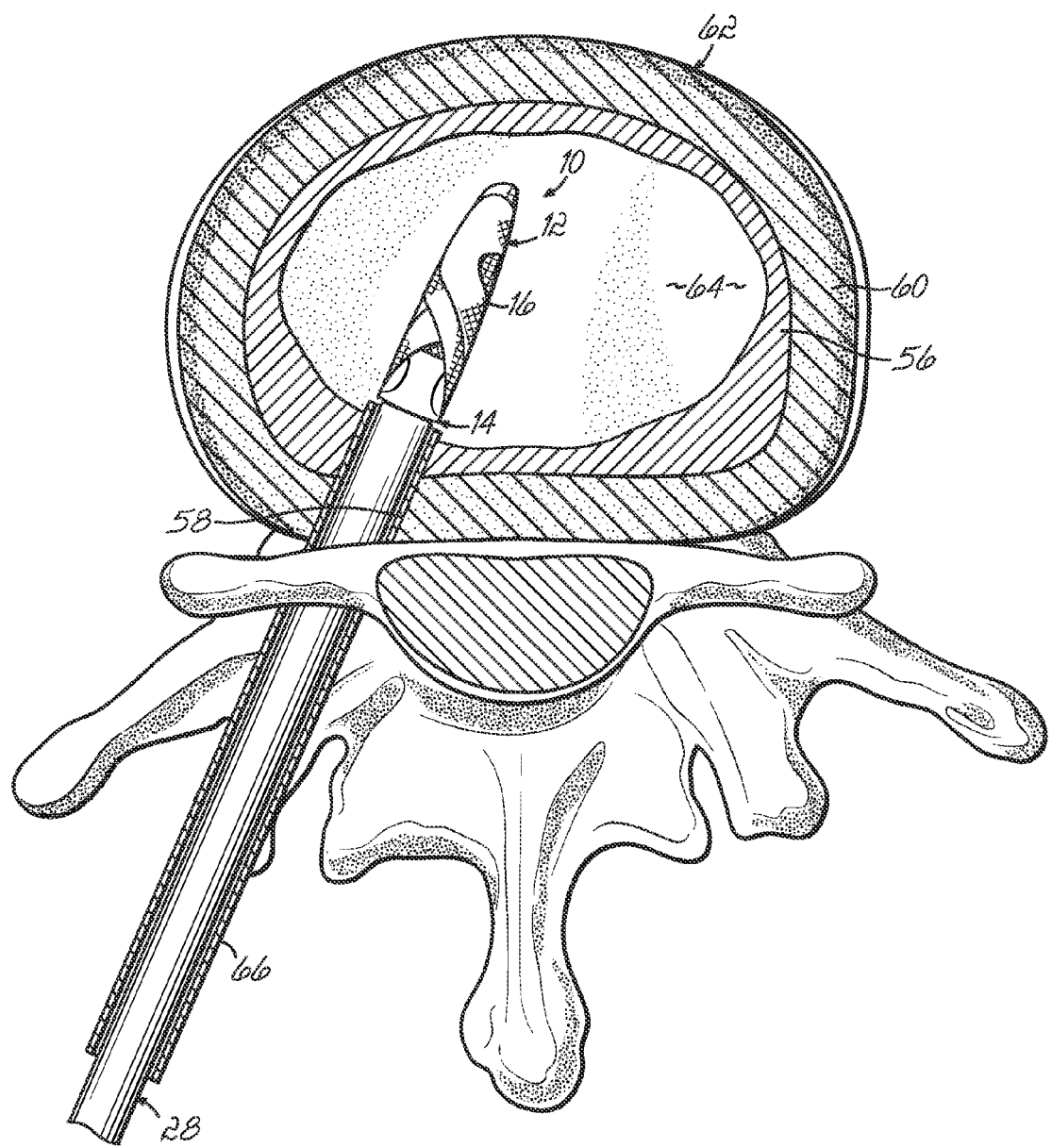
FIG. 7 depicts a cross-sectional view taken along a transverse plane through an intervertebral disc illustrating a delivery cannula inserted therein for delivery of one embodiment of the interbody device with the member shown wrapped around a coupler.

With reference generally to FIGS. 7-11, one method of using the system or treating a spine is illustrated. As one skilled in the art will appreciate, a discectomy involves resection of a portion of a nucleus 56 via an incision 58 made in an annulus 60 of a disc 62 thereby creating a disc space 64. With reference to FIG. 7, the method includes placing one embodiment of the interbody device 10 within the disc space 64. By way of example, in one embodiment of the system, a delivery cannula 66 is inserted through the incision 58 and into the disc space 64. The interbody device 10 with the member fill tube 28 inserted into the coupler 14 is inserted either simultaneously with the delivery cannula 66 through the incision 58 or following initial insertion of the delivery cannula 66 through the incision 58, i.e. as a separate insertion step. The coupler 14 and annular member 12 may cooperate somewhat like a trocar, known in the art, to ease passage of the coupler 14, annular member 12, and delivery cannula 66 through the incision 58. The coupler 14 and annular member 12 may also pass through the delivery cannula 66 into the disc space 64. It will be appreciated that the annular member 12 may be folded, wrapped, or otherwise configured for insertion through the delivery cannula 66.

Figure 8:
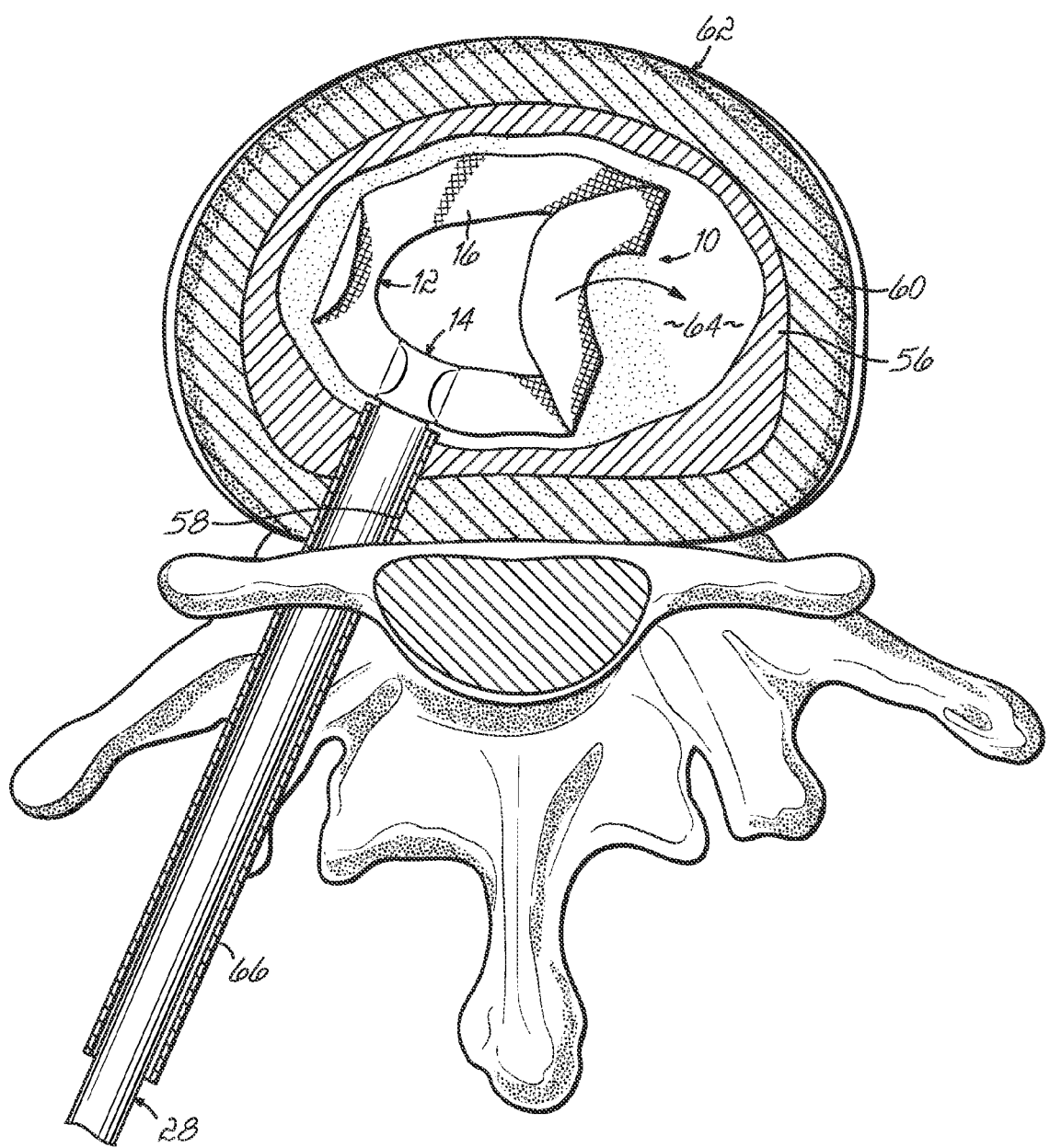
FIG. 8 depicts one method of placing an interbody device within the disc of FIG. 7.
Figure 9:
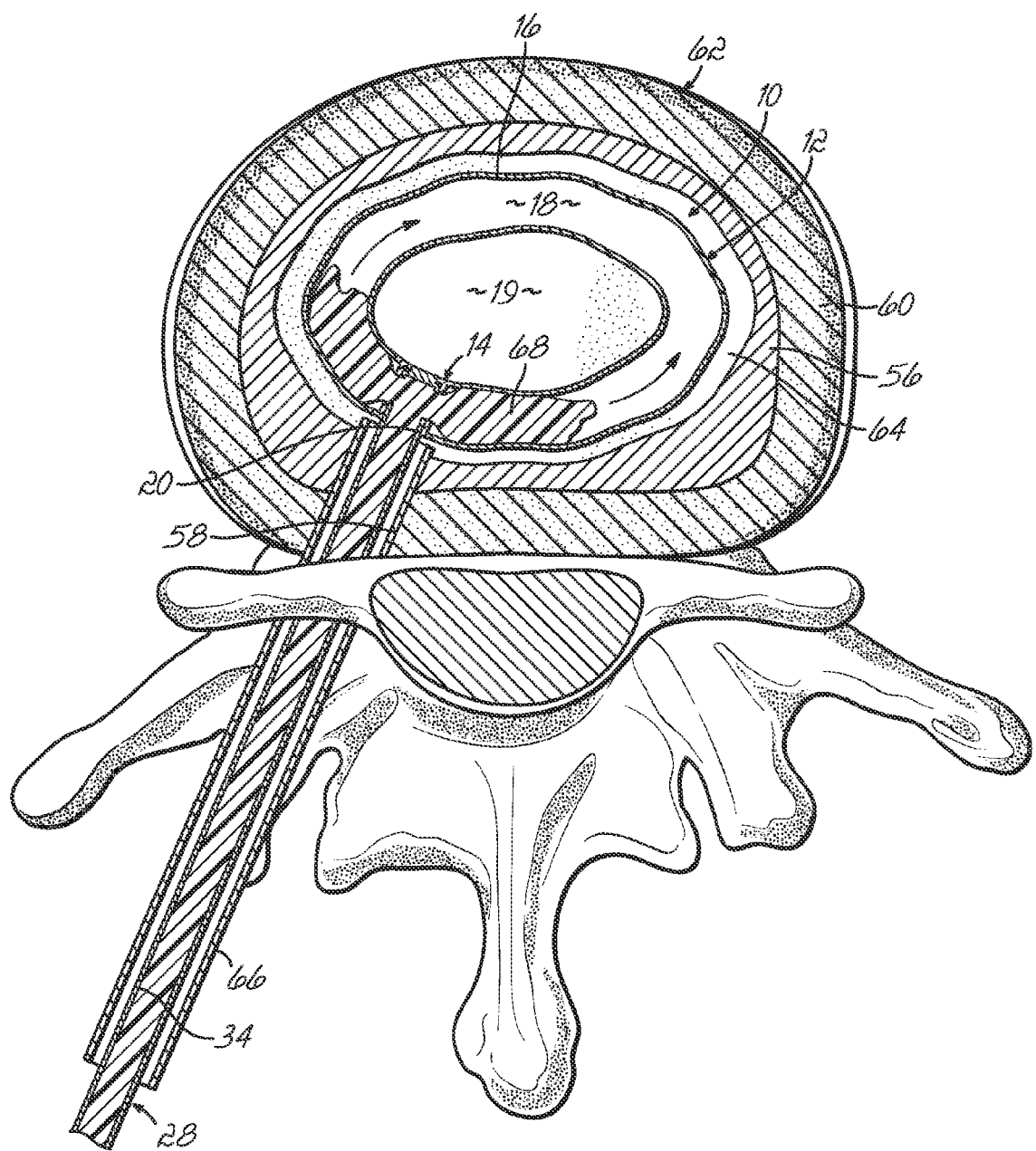
FIG. 9 depicts one method of providing a first filler material into the member of FIG. 8.
Figure 12:
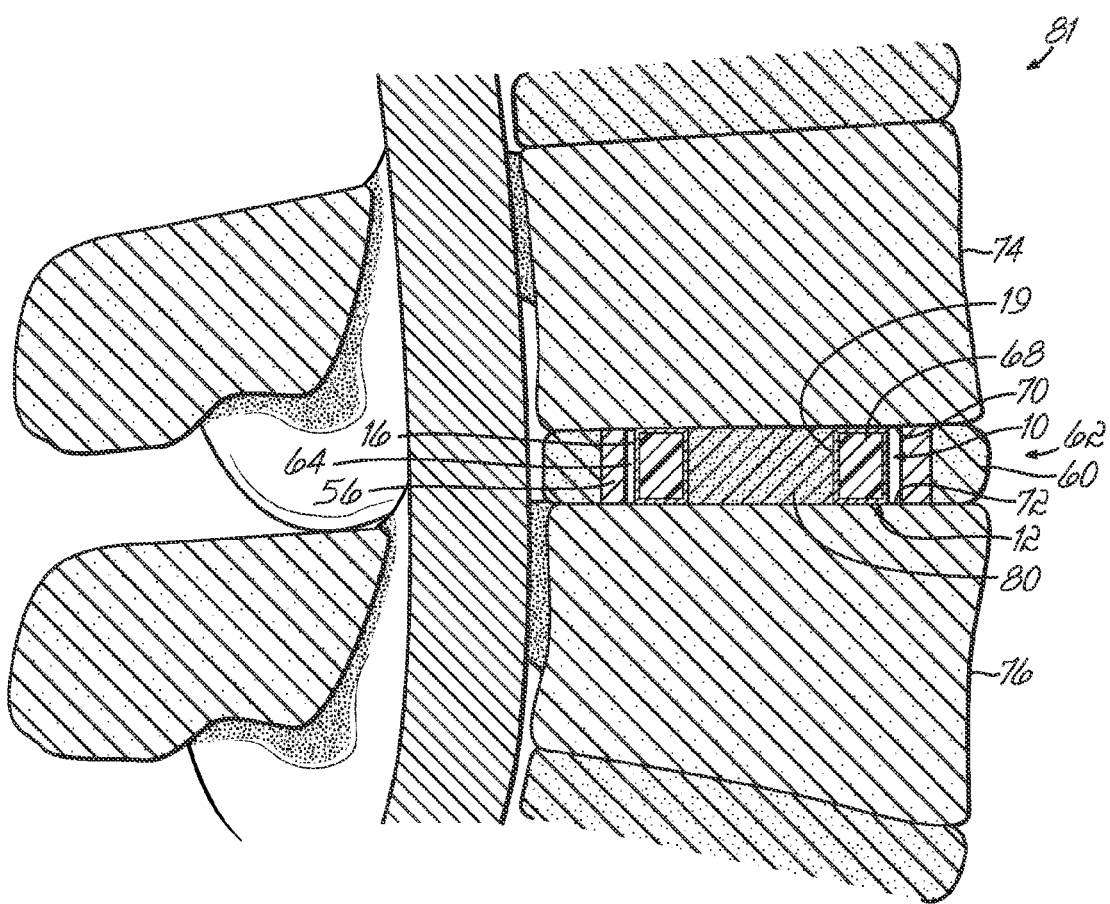
FIG. 12 depicts a cross-sectional view taken along a sagittal plane through a spine illustrating one embodiment of the interbody device placed within a disc and following injection of the first filler material and the second filler material therein.

With reference now to FIG. 8, the annular member 12 in an unexpanded state is unfolded within the disc space 64. Once placed, and with reference to FIG. 9, a first filler material 68 is injected into the opening 40 in the distal end 36 (not shown) of the member fill tube 28. The first filler material 68 passes through the first passage 34 through the coupler 14 and into the internal volume 18 of the annular member 12 (one possible flow pattern is illustrated in FIG. 9). While FIG. 9 clearly illustrates flow of the first filler material 68 through both sides of the coupler 14, that is through aligned holes 24, 42 and 26, 44 (shown in FIG. 5), it will be appreciated that only one coupler side hole 24 or 26 may permit injection of the first filler material 68 into the internal volume 18. In another embodiment, the annular flange 32 shown most clearly in FIG. 5, may prevent the first filler material 68 from being accidentally injected into the interior cavity 19 should the member fill tube 28 be accidentally removed following insertion of the delivery cannula 66, annular member 12, and member fill tube 28 through the incision 58 and thus requiring reinsertion of the member fill tube 28. Expanding the annular member 12 may facilitate distraction of adjacent vertebrae and possibly decompression. The degree of distraction may depend upon the pressure used to inject the first filler material 68 and the material of the flexible wall 16. Also, as previously noted, the annular member 12 may excrete a portion of the first filler material 68. Therefore, if the annular member 12 contacts the endplates 70, 72 of the adjacent vertebrae 74, 76 as shown in FIG. 12, the first filler material 68 may facilitate bonding of the annular member 12 to the endplates 70, 72.

Returning to FIG. 9, once the annular member 12 is sufficiently filled, the interior cavity 19 is formed. The member fill tube 28 may then be withdrawn. During withdrawal of the member fill tube 28, the coupler 14 may cooperate with the member fill tube 28 to substantially prevent the first filler material 68 from entering the coupler 14. In other words, any residual first filler material 68 within the member fill tube 28 may be prevented from building up within the coupler 14. In one method, once the member fill tube 28 is withdrawn from the coupler 14, the first filler material 68 may then be hardened or permitted to harden. In another embodiment, the first filler material 68 is an elastomeric material that may or may not harden following placement of the fill material 68 into the internal volume 18.

In another method, the first filler material 68 is an in-situ curable material that hardens prior to removal of the member fill tube 28. The coupler 14 may aid removal therefrom by limiting contact of the fill material 68 with the member fill tube 28. Thus, slight movement, e.g., rotation, of the member fill tube 28 may break any connectivity between the in-situ curable first filler material 68 and the member fill tube 28.

By way of example and not limitation, the first filler material 68 may include bioresorbable materials; elastic materials, such as, polyurethane, silicone rubber, in-situ curable polymer (most likely an elastomer), and PVA (polyvinyl alcohol) hydrogel; or other hydrogels, or may comprise poly(lactic acid), poly(glycolic acid), p-dioxanone fibers, polyarylethyl, polymethylmethacrylate, polyurethane, amino-acid-derived polycarbonate, polycaprolactone, aliphatic polyesters, calcium phosphate, unsaturated linear polyesters, vinyl pyrrolidone, polypropylene fumarate diacrylate, polymethylmethacrylate (PMMA), bis-GMA polymer, hydrogel polyurethane, polyacrylamides, a hydrogel or combinations thereof, or other biologically compatible polymer capable of supporting axial loads transmitted through the spinal column.

Figure 10:
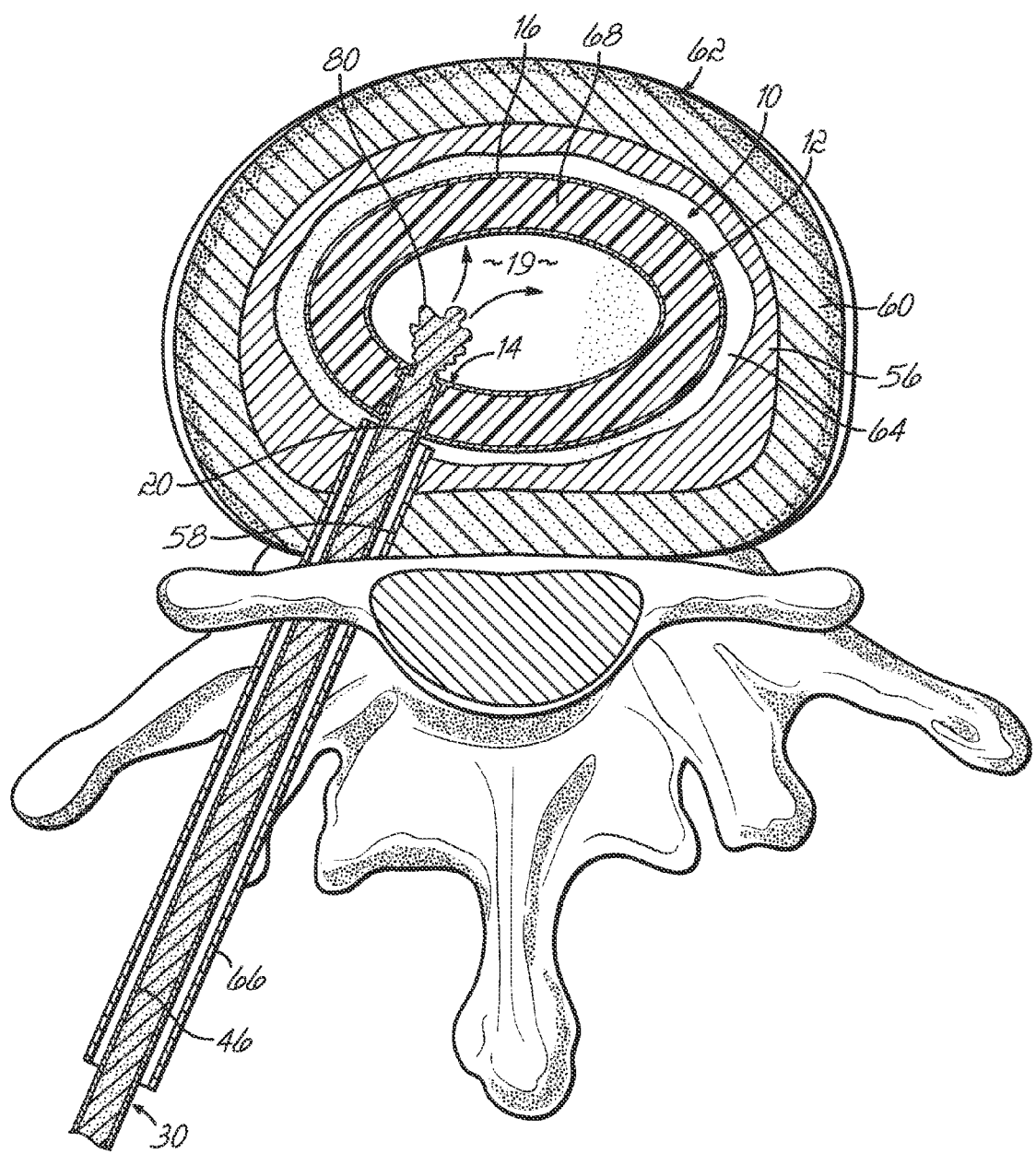
FIG. 10 depicts one method of providing a second filler material within the member following providing the first filler material of FIG. 9.

In one method, once the member fill tube 28 in FIG. 9 is withdrawn from the coupler 14, the cavity fill tube 30 may be inserted into the coupler 14, as shown in FIG. 10. The coupler 14 may also aid in the insertion of the cavity fill tube 30 by keeping the first access point 20 free of the first filler material 68. In another embodiment, the annular flange 32, best shown in FIGS. 5 and 6, may prevent the cavity fill tube 30 from being thrust into the interior cavity 19 and potentially rupturing the flexible wall 16. Once the cavity fill tube 30 is inserted into the coupler 14, a second filler material 80 is injected into the opening 52 in the distal end 48 (not shown) of the cavity fill tube 30. The second filler material 80 passes through the second passage 46, through the coupler 14, and into the interior cavity 19. In one embodiment, the second filler material 80 fills the interior cavity 19 formed by the interbody device 10 to contact each endplate 70, 72 of each vertebrae 74, 76, as shown in FIG. 12.

As previously described, the cavity fill tube 30 is inserted into the delivery cannula 66 to engage the coupler 14, usually without visual assistance, though guide wires (not shown) may assist the surgeon in inserting the cavity fill tube 30 into the coupler 14. In those instances where no visual assistance is available, the annular flange 32, shown most clearly in FIG. 6, may provide some tactile sensation that the cavity fill tube 30 has seated within the coupler 14. The annular flange 32 may prevent the surgeon from inadvertently inserting the cavity fill tube 30 and damaging the annular member 12. Alternatively, since the surgeon is expecting the cavity fill tube 30 to seat within the coupler 14, the lack of the docking or seating sensation may prevent the surgeon from inadvertently injecting the second filler material 80 into the disc space 64. As with removal of the member fill tube 28 in FIG. 5, one skilled in the art will appreciate that the coupler 14 may ease withdraw of the cavity fill tube 30 by substantially preventing the first filler material 68 from contaminating the cavity fill tube 30 if the first filler material 68 has not sufficiently hardened prior to its removal.

Figure 11:
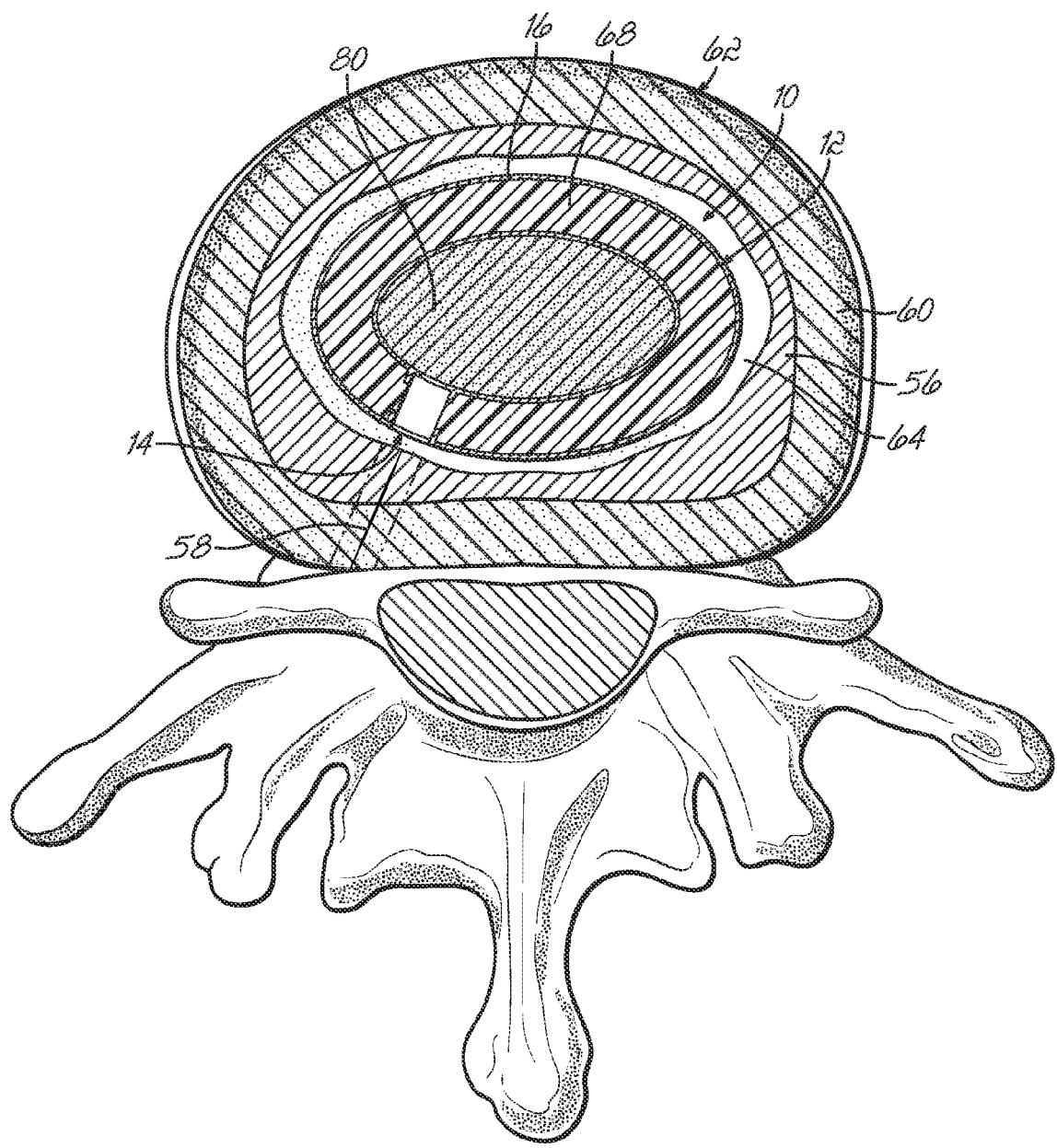
FIG. 11 depicts one embodiment of the interbody device of FIG. 10 following removal of the delivery cannula and closure of the incision in the annulus.
Figure 18:
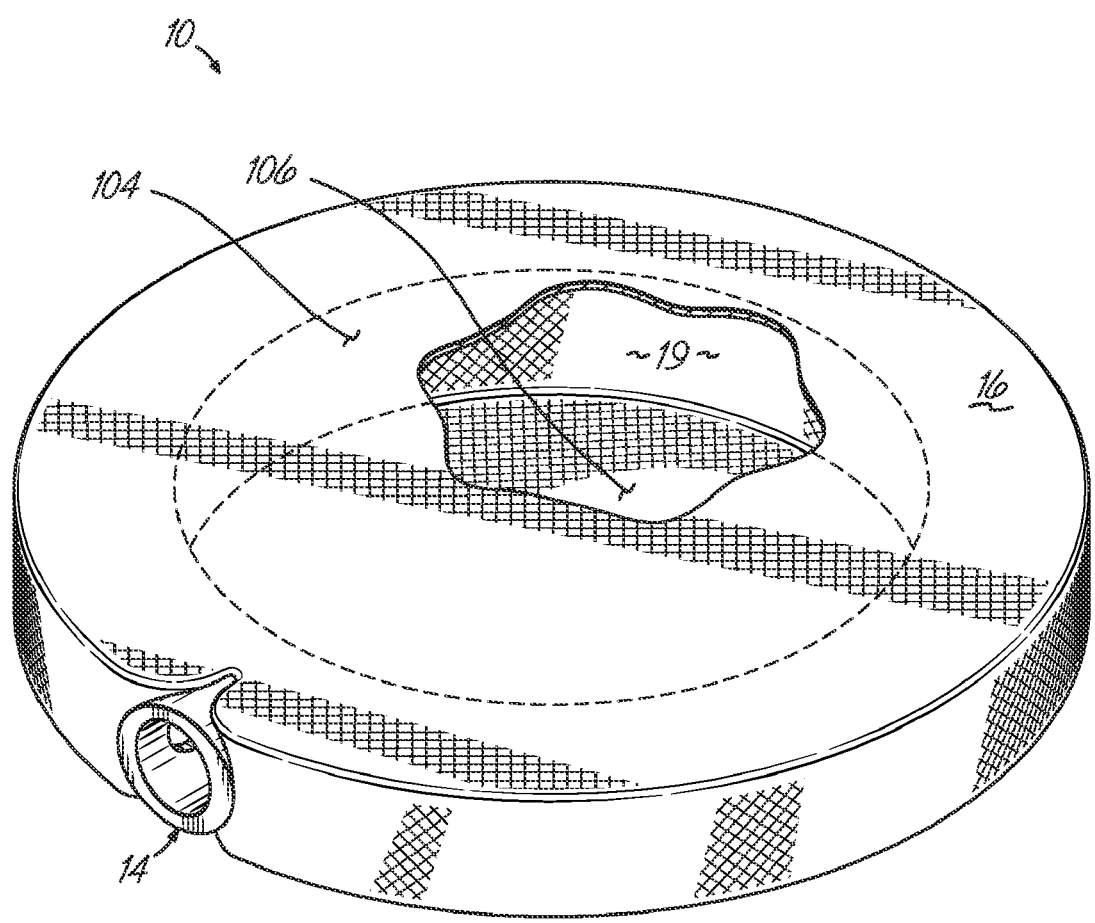
FIG. 18 is a perspective view of one embodiment of an interbody device shown with a member in an expanded state.

As shown in FIG. 11, the cavity fill tube 30 is removed once the interior cavity 19 is filled with the second filler material 80. The delivery cannula 66 is also removed. The incision 58 in the annulus 60, as well as other necessary incisions in the surrounding tissue, are closed. FIGS. 7-11 illustrate a posterior entry into the disc 62; however, as previously mentioned, other approaches are also possible. For example, insertion approaches may include a posterolateral approach, transformational approach, anterior approach, anterolateral transpsoatic approach, anterior lateral retroperitoneal approach, and others. Also, while FIGS. 7-11 illustrate placement of only one interbody device 10 in the disc space 64, it is possible to place multiple interbody devices 10 within the disc space 64 depending on the size and shape of the interbody device 10. Optionally, as depicted in FIG. 18, the second filler material 80 can be contained within the interior cavity 19 by including or weaving additional material into the interbody device 10 to create a barrier such as top and bottom walls 104, 106 that cover the openings in the interior cavity 19. These portions of the interbody device 10 may be shaped to the shape of the vertebral endplates.

With reference now to FIG. 12, one embodiment of the interbody device 10 is shown following placement and injection of the first filler material 68 into the annular member 12 and the second filler material 80 into the interior cavity 19. Therefore, following placement of the first filler material 68 and the second filler material 80, the interbody device 10 may provide support to the spine 81 by maintaining separation of the adjacent vertebrae 74, 76. In one embodiment, the second filler material 80 is a fusion promoting material that bonds to the endplates 70, 72 of the adjacent vertebrae 74, 76. In another embodiment, the second filler material 80 is an elastomeric material that may be more elastic than the first filler material 68. In an alternative embodiment, the first elastomeric material may be more than elastic than the second elastomeric material. By way of example, filling the annular member 12 with elastomeric materials may allow it to mimic the natural kinematics associated with a healthy disc. Exemplary materials include, bioresorbable materials; elastic materials, such as, polyurethane, silicone rubber, in-situ curable polymer (most likely an elastomer), and PVA (polyvinyl alcohol) hydrogel; or other hydrogels, or may comprise poly (lactic acid), poly(glycolic acid), p-dioxanone fibers, polyarylethyl, polymethylmethacrylate, polyurethane, amino-acid-derived polycarbonate, polycaprolactone, aliphatic polyesters, calcium phosphate, unsaturated linear polyesters, vinyl pyrrolidone, polypropylene fumarate diacrylate, polymethylmethacrylate (PMMA), bis-GMA polymer, hydrogel polyurethane, polyacrylamides, a hydrogel or combinations thereof, or other biologically compatible polymer capable of supporting axial loads transmitted through the spinal column.

Figure 13:
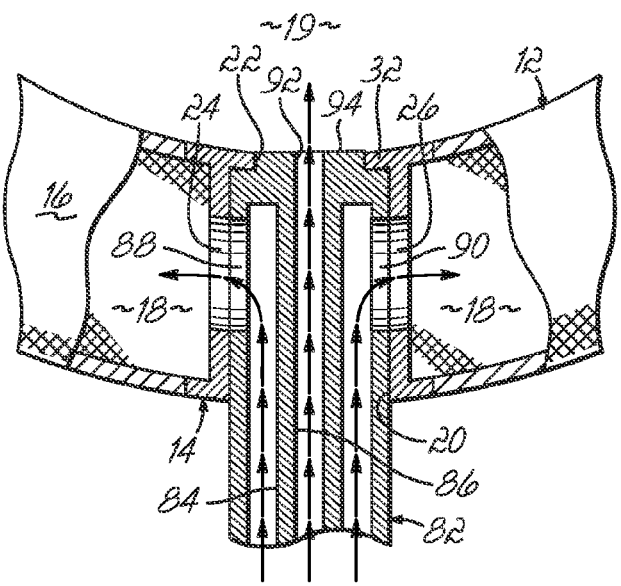
FIG. 13 depicts an enlarged, partial cross section of an embodiment of a dual lumen fill tube inserted into the embodiment of the coupler of FIG. 2.

In another exemplary embodiment, the system may comprise a dual lumen fill tube 82. As shown in FIG. 13, the dual lumen fill tube 82 defines a first passage 84 and a second passage 86. The dual lumen fill tube 82 is inserted into the coupler 14 with the first passage 84 in fluid communication with the internal volume 18 via alignment of the first and second coupler side holes 24, 26 with a first tube side hole 88 and a second tube side hole 90, respectively. It will be appreciated that only one of the side holes 88 or 90 or other opening may be necessary to fill the internal volume 18.

The second passage 86 of the dual lumen fill tube 82 is in fluid communication with the interior cavity 19 via an axial port 92. By way of example only, and not limitation, the first passage 84 may be concentric around the second passage 86. It will be appreciated, however, that other configurations may be used, e.g. side-by-side passages. As shown in FIG. 13, the arrows illustrate flow directions for both the first filler material 68 and the second filler material 80 into the internal volume 18 and the interior cavity 19, respectively. In one embodiment, providing the first filler material 68 and the second filler material 80 may proceed simultaneously, though the rate of introduction of the first filler material 68 may differ from the rate of introduction of the second filler material 80. In another embodiment, the internal volume 18 may be filled to begin formation of the interior cavity 19. The second filler material 80 may then immediately follow once a sufficient portion of the interior cavity 19 has formed. In yet another embodiment, a proximal end 94 of the dual lumen fill tube 82 cooperates with the annular flange 32 of the coupler 14, as previously described with respect to the member fill tube 28 in FIG. 5 and the cavity fill tube 30 in FIG. 6.

Figure 14:
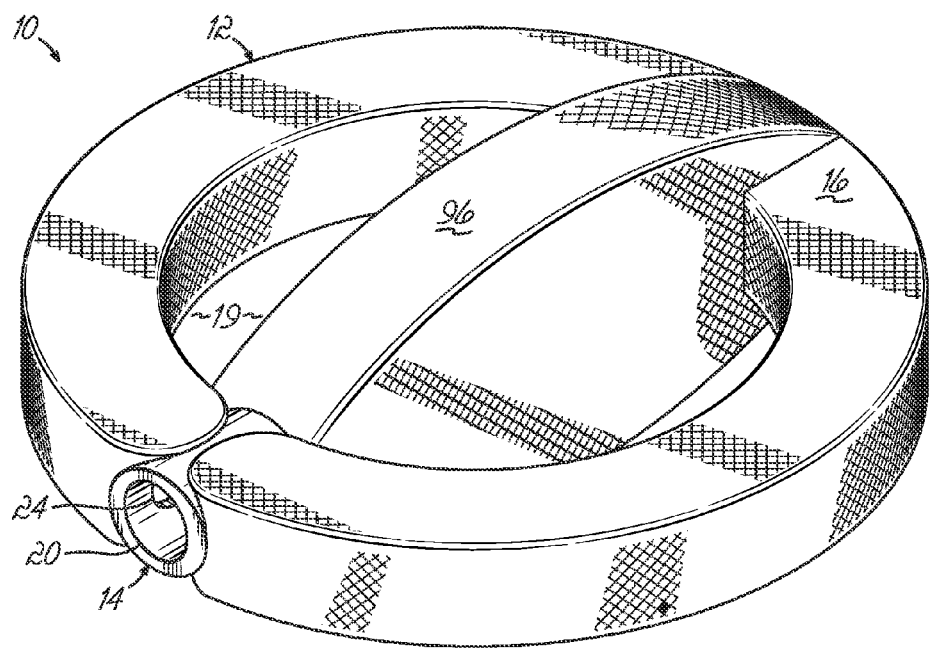
FIG. 14 is a perspective view of another embodiment of the interbody device having a keel contiguously formed with the member.
Figure 15:
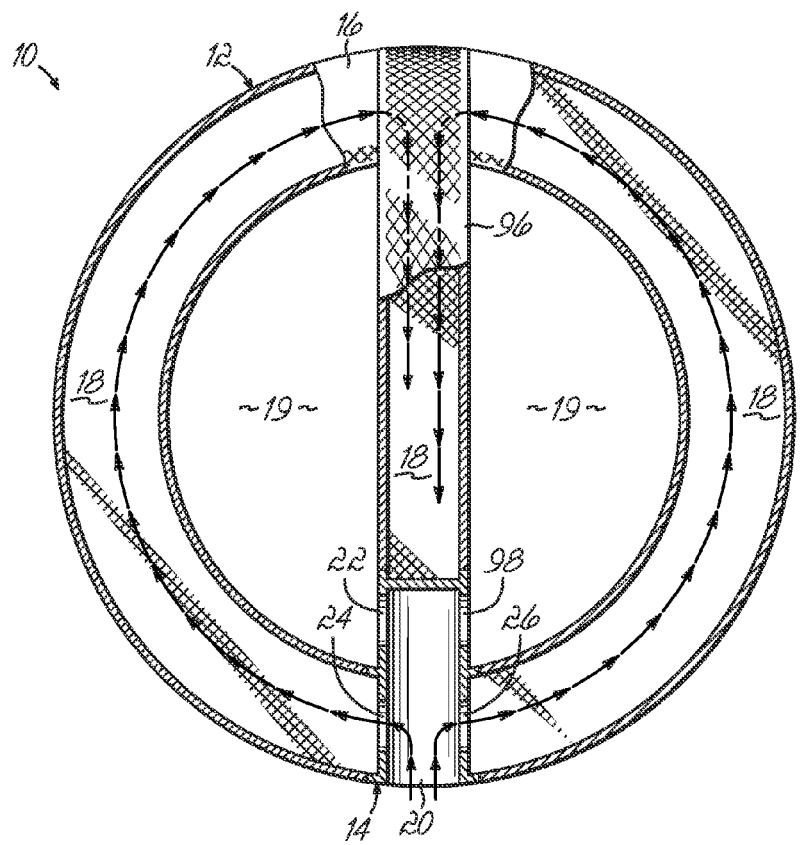
FIG. 15 is a plan view of the interbody device of FIG. 14 with a partial cross section of another embodiment of the coupler and the member.
Figure 16:
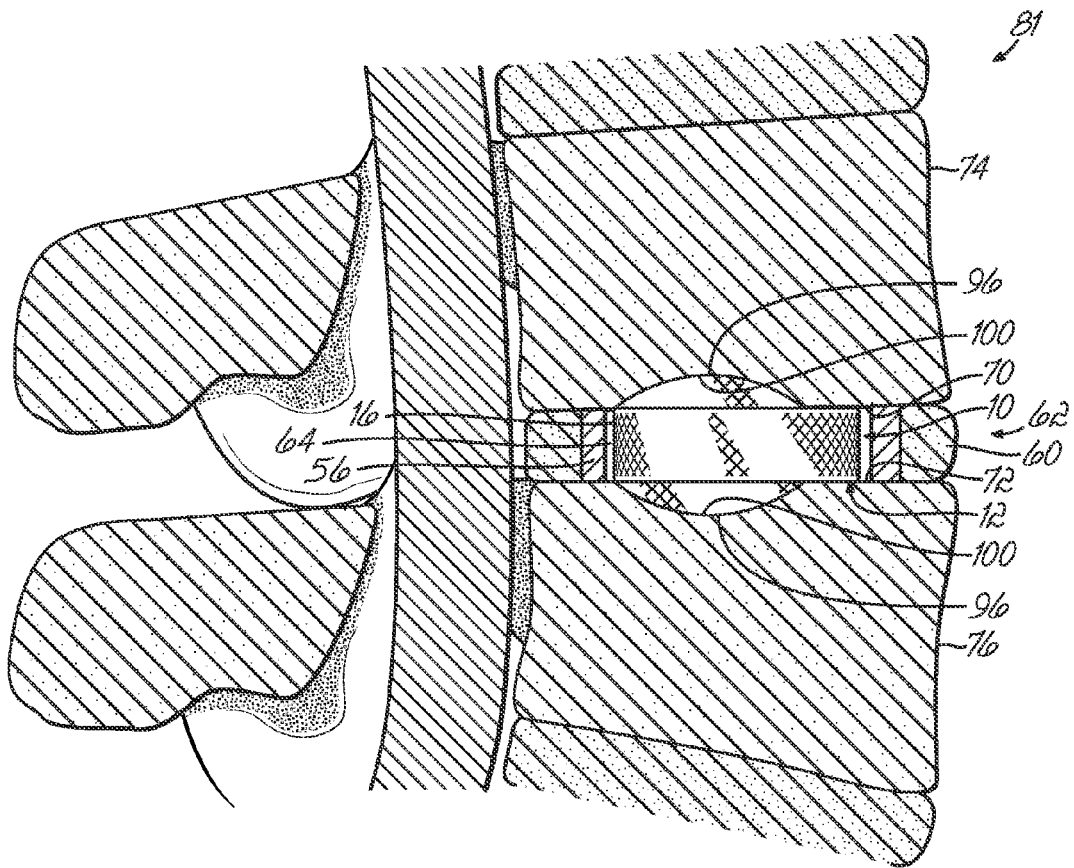
FIG. 16 depicts a cross-sectional view taken along a sagittal plane through a spine with the embodiment of the interbody device of FIG. 14 placed within a disc and following injection of the first filler material and the second filler material.

Another exemplary embodiment of the interbody device 10 is shown in FIGS. 14, 15, and 16. The annular member 12 of FIG. 14 has a keel 96 projecting substantially vertically from the annular member 12. The keel 96 may be formed of the flexible wall 16 and thus surround the internal volume 18, as shown in FIG. 15. In one embodiment, the coupler 14 is elongated with a third access point 98. The second and third access points 22, 98 may be positioned on opposing sides of the coupler 14 to provide access to the interior cavity 19 adjacent the projecting keel 96. Similar to previously described embodiments of the annular member 12, the annular member 12 of FIG. 14 is filled with the first filler material 68 through the first and second coupler side holes 24, 26, for example, when they are aligned with the first and second tube side holes 42, 44 of the member fill tube 28 shown in FIG. 3, or through the first and second tube side holes 88, 90 of the dual lumen fill tube 82 shown in FIG. 13. However, the first filler material 68 also fills the keel 96, for example, through its end opposite the coupler 14, shown in FIG. 15. The keel 96 may, for example, be a perpendicular extension of the annular member 12 that expands to project in a vertical direction. In one embodiment, the keel 96 may partition the interior cavity 19 into multiple components. As shown in FIG. 15, the interior cavity 19 may comprise sinistral and dextral portions. Thus, during injection of the second filler material 80, the second filler material 80 passes out of the coupler 14 into one of the sinistral or dextral portions of the interior cavity 19 via the second or third access points 22, 98, respectively.

With reference now to FIG. 16, the keel 96 may cooperate with depressions, such as channels 100, formed in the endplates 70, 72 of the vertebrae 74, 76, respectively. Thus, as the first filler material 68 is injected into the annular member 12, the keel 96 may expand into one or more of the channels 100. It will be appreciated that the keel 96 may cooperate with the channels 100 to reduce the risk of migration of the interbody device 10 from its initial position. It will also be appreciated that the keel 96 may have other configurations projecting toward one or both endplates 70, 72. The channels 100 may be machined into endplates 70, 72 prior to insertion of the interbody device 10 to accept the projecting portion, such as the keel 96.

Figure 17:
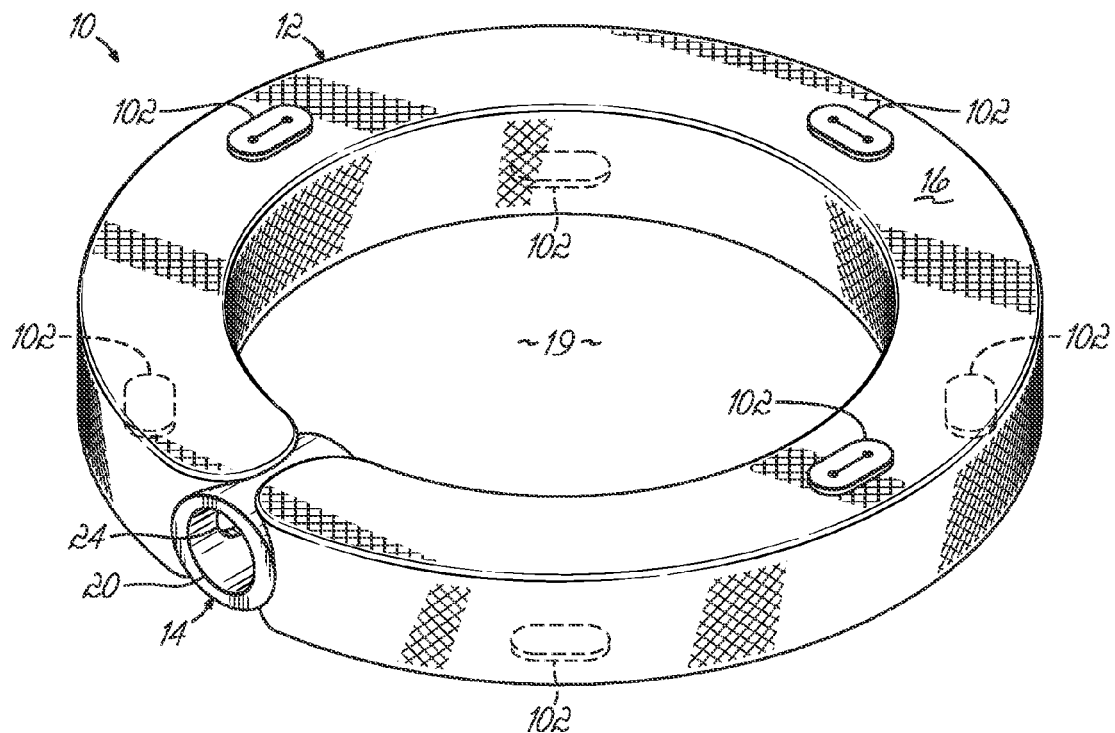
FIG. 17 is a perspective view of another embodiment of the interbody device having a plurality of endplate anchors secured to the member thereof.

FIG. 17 illustrates another exemplary embodiment of the interbody device 10. As shown, the annular member 12 is shown in an expanded state having a plurality of endplate anchors 102. The endplate anchors 102 may be attached to the flexible wall 16 such that they may contact adjacent vertebrae. Thus, as the annular member 12 expands with the first filler material 68, one or more of endplate anchors 102 may then contact one endplate 70, 72 of the adjacent vertebra 74, 76. By way of example, the endplate anchors 102 may be natural or synthetic bone, a porous metal such as TRABECULAR METAL™ sold by Zimmer Spine, Inc. of Edina, Minn., or other compatible material that is osteoconductive. The endplate anchor 102 may also provide additional frictional engagement of the interbody device 10 with one of the endplates 70, 72, which may stabilize the annular member 12 for subsequent injection of the second filler material 80.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. An orthopedic system adapted for insertion between adjacent vertebrae in a spine, the system comprising:
    an annular member having a flexible wall surrounding an internal volume, the annular member having first and second ends and being adapted to expand when filled with a first filler material thereby forming an interior cavity;
    a coupler positioned between and spacing apart the first and second ends of the annular member, the coupler connecting the first and second ends of the annular member, the coupler comprising a rigid material, the coupler having a first access point, a second access point, a first coupler side hole, and an optional second coupler side hole adapted to removably receive one or more fill tubes that cooperate with the first and optional second coupler side holes to direct the first filler material into the internal volume and that cooperate to direct a second filler material into the interior cavity, wherein the coupler includes an annular flange;
    a member fill tube defining a first passage and adapted for removable cooperation with the coupler via the first access point, the member fill tube having a closed proximal end and one or more side holes adjacent the proximal end, the member fill tube configured such that when the member fill tube is inserted into the coupler, the closed proximal end abuts the annular flange and is prevented from extending through the second access point, and the one or more side holes of the member fill tube are in fluid communication with the internal volume via the first coupler side hole, and the optional second coupler side hole; and
    a cavity fill tube defining a second passage and adapted for removable cooperation with the coupler via the first access point and the second access point such that when the cavity fill tube is inserted into the coupler, an opening at a proximal end of the cavity fill tube is in fluid communication with the interior cavity via the second passage and the second access point, wherein the proximal end of the cavity fill tube is sized such that the annular flange on the coupler prevents the cavity fill tube from extending through the second access point.

2. The system of claim 1 further including a plurality of endplate anchors attached to the flexible wall, the endplate anchors being adapted to engage an endplate of the adjacent vertebrae.

3. The system of claim 2 wherein the first filler material comprises a first elastomeric material and the second filler material comprises a second elastomeric material that is more elastic than the first elastomeric material.

* * * * *

UNITED STATES PATENT AND TRADEMARK OFFICE
CERTIFICATE OF CORRECTION

| | | |
|---|---|---|
| PATENT NO. | : 8,043,381 B2 | Page 1 of 1 |
| APPLICATION NO. | : 11/926975 | |
| DATED | : October 25, 2011 | |
| INVENTOR(S) | : Hugh D. Hestad et al. | |

It is certified that error appears in the above-identified patent and that said Letters Patent is hereby corrected as shown below:

Column 8
Line 2-3, delete "transformational", and insert therefore -- transforaminal --.

Signed and Sealed this
Sixth Day of December, 2011

David J. Kappos
*Director of the United States Patent and Trademark Office*